US00PP09352P

United States Patent [19]

Guillou et al.

[11] Patent Number: Plant 9,352

[45] Date of Patent: Oct. 31, 1995

[54] GERANIUM PLANT NAMED 'GUIMONGOL'

[75] Inventors: Jacques Guillou; Bernard Guillou; Maurice Guillou, all of Saint-Malo, France

[73] Assignee: Ets. Guillou Freres, Saint-Malo, France

[21] Appl. No.: 353,329

[22] Filed: Dec. 5, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A distinct cultivar of geranium plant named Guimongol particularly characterized by the combined features of pink semi-double flowers, medium green foliage with weak zonation, and compact bushy plant habit.

1 Drawing Sheet

The present invention comprises a new and distinct cultivar of geranium, botanically known as *Pelargonium peltatum l'Hert,* and hereinafter referred to by the cultivar name Guimongol.

Guimongol is a product of a planned breeding program which had the objective of creating new ivy geranium cultivars with pink flower color, and compact and well branched growth habit.

Guimongol was originated from a hybridization made by the inventors in Saint-Malo, France in 1984. The female and male parents were unnamed pink semi-double hybrids from the proprietary collection of the joint inventors.

Guimongol was discovered and selected as one flowering plant within the progeny of the stated cross by the inventors in May 1985 in a controlled environment in Saint-Malo, France.

The first act of asexual reproduction of Guimongol was accomplished when vegetative cuttings were taken from the initial selection in 1986 in a controlled environment in Saint-Malo, France, by or under the supervision of the inventors.

Horticultural examination of plants grown from cuttings initiated in Hillscheid, Federal Republic of Germany, in May 1991 and continuing thereafter has demonstrated that the combination of characteristics as herein disclosed for Guimongol are firmly fixed and are retained through successive generations of asexual reproduction.

Guimongol has not been observed under all possible environmental conditions. The phenotype may vary significantly with variations in environment such as temperature, light intensity and day length, without, however any variations in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Guimongol, which in combination distinguish this geranium as a new and distinct cultivar:

1. Pink semi-double flowers.
2. Medium green foliage.
3. Zonation forms a ring near the base of the leaf.
4. Compact plant habit.
5. Good branching habit.

Of the many known commercial cultivars, the most similar in comparison to Guimongol is the unpatented cultivar Salmon Queen. Reference is made to attached Chart A which compares certain characteristics of Guimongol to those same characteristics of Salmon Queen. In general comparison to Salmon Queen, Guimongol has a lighter flower color, more compact plant habit and a different shape of leaf.

The accompanying photographic drawing shows typical flower and foliage characteristics of Guimongol, with colors being as true as possible with illustrations of this type.

In the following description color references are made to The Royal Horticultural Society Color Chart. The color values were determined indoors in May from plants grown in greenhouses in Hillscheid, Federal Republic of Germany.

Classification:

*Botanical.*—A hybrid of the species *Pelargonium peltatum l'Hert.*

*Commercial.*—Ivy geranium, cv. Guimongol.

Inflorescence:

*Umbel.*—Shape — Nearly semi-spherical. Average diameter — 95 mm. Average depth — 45 mm. Peduncle length — 164 mm. Pedicel length — 25 mm. Pedicel color — Green and light red pedicels with "knots". Number of flowers per umbel — 15–20.

*Corolla.*—Average diameter — 45 mm. Form — Semi-double. Average number of petals — 6–9. Average number of petaloids — 2–4. Color (general tonality from a distance of three meters) — Pink. Color of upper petals — 67 C, lighter near margin. Color of lower petals — 58 B, lighter near margin. Markings (only on upper petals) — Dark red veins and carmine macula. Color of lower surface of petals — 55 B. Color of sepals — Light green. Number of sepals — 5.

*Bud.*—Shape — Narrow elliptic. Color (adaxial) — Green, no anthocyanine. Color (abaxial) — Salmon Pink.

*Reproductive organs.*—Androecium — 3–7 fertile anthers, white filaments, and orange pollen. Gynoecium — 5–6 lobed stigma, red style and stigma; fruit or seed has not been observed.

*Spring flowering response period.*—In Hillscheid, Federal Republic of Germany in 1993 plants had on average 1.4 flowers opened 15 weeks after planting of unrooted cuttings (pinched plants).

*Outdoor flower production.*—The flower count in 1992 in Hillscheid, Federal Republic of Germany indicated between 80 and 90 flowers per plant for May through August observation period.

*Durability.*—Shatter resistance good.

Plant:

*Foliage.*—Form — Ivy shaped. Margin — Entire. Size of leaf — 75–80 mm. Color of upper surface — Green, approximately 137 C. Color of zonation —

Brown, approximately 166 A; sometimes hardly visible. Tolerance of botrytis — Good. Surface — Smooth; dull, not reflective.

*General appearance and form.*—Internode length — 3–4 cm. Branching pattern — 5.2 branches per plant. Height — 50 cm in August.

CHART A

| CHARACTERISTIC | GUIMONGOL | SALMON QUEEN |
|---|---|---|
| Flower color, upper petals | R.H.S. 67 C-D | R.H.S. 58 B-C |
| Maculas of upper petals | Carmine Red | Dark red |

CHART A-continued

| CHARACTERISTIC | GUIMONGOL | SALMON QUEEN |
|---|---|---|
| Zonation | Weak | Very weak |
| Internodes | 3–4 cm | 4–6 cm |
| Shape of leaf | Normal ivy shape, slightly pointed tips. | Weak degree of lobing, rounded tips. |

It is claimed:

1. A new and distinct cultivar of geranium plant named Guimongol, as illustrated and described.

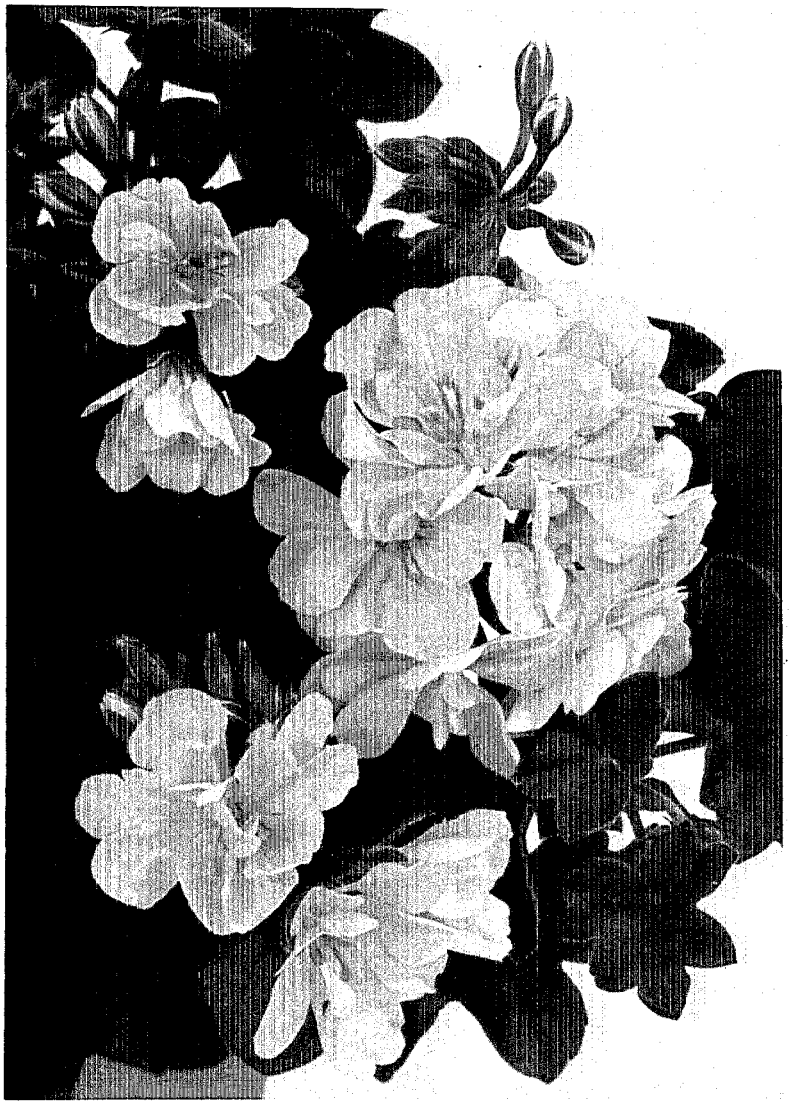

* * * * *